United States Patent [19]

Chase et al.

[11] Patent Number: 5,092,678
[45] Date of Patent: Mar. 3, 1992

[54] ON-LINE SHEET FORMATION CHARACTERIZING METHOD AND DEVICE

[75] Inventors: Lee M. Chase, Los Gatos; Jorma Orkosalo, San Jose; Kent M. Norton, Saratoga, all of Calif.

[73] Assignee: Measurex Corporation, Cupertino, Calif.

[21] Appl. No.: 930,142

[22] Filed: Nov. 12, 1986

[51] Int. Cl.$^5$ .............................................. G01N 21/86
[52] U.S. Cl. ..................................... 356/429; 356/432; 250/559; 250/571
[58] Field of Search ............... 356/429, 430, 432, 440, 356/443; 250/559, 571, 572; 350/273, 274

[56] References Cited

U.S. PATENT DOCUMENTS

| | | | |
|---|---|---|---|
| 3,114,791 | 12/1963 | Zabel et al. | 356/429 |
| 3,135,819 | 6/1964 | Quinn | 350/274 |
| 3,228,282 | 1/1966 | Barker | 356/429 |
| 3,469,104 | 9/1969 | Hector | 356/430 |
| 3,525,871 | 8/1970 | Lehtinen | 356/430 |
| 3,824,021 | 7/1974 | Axelrod et al. | 250/571 X |
| 3,900,265 | 8/1975 | Merlen et al. | 250/572 X |
| 4,288,160 | 9/1981 | Lodzinski | 356/429 X |
| 4,453,404 | 6/1984 | Powell et al. | 73/159 |
| 4,455,090 | 6/1984 | Roberts | 356/448 |
| 4,644,174 | 2/1987 | Ouellette et al. | 250/559 |
| 4,648,712 | 3/1987 | Brenholdt | 356/429 |
| 4,776,538 | 9/1988 | Orkosalo | 356/429 |

FOREIGN PATENT DOCUMENTS

| | | | |
|---|---|---|---|
| 0133467 | 1/1979 | German Democratic Rep. | 250/571 |
| 0162844 | 9/1983 | Japan | 250/572 |
| 2147413 | 5/1985 | United Kingdom . | |

OTHER PUBLICATIONS

Patent Abstracts of Japan, vol. 6, No. 229 (P-155) (1107), Nov. 16, 1982 (Shimaau Seisakusho K.K.) 8/13/82, 57-131007.
Specific Perimeter-A Graininess Parameter for Formation and Print-Mottle Textures by B. D. Jordan and H. G. Nguyen, published in "Papieri Ja Pau", Jun.-Jul. 1986, vol. 67, Issue 6-7.
Using a Beta Radiographic Method, Bo Norman and Douglas Wahren, Swedish Forest Products Research Laboratory, Stockholm, 1974.
A Comprehensive Method for the Description of Mass Distribution in Sheets and Flocculation and Turbulence in Suspensions, Bo Norman and Douglas Wahren, Swedish Forest Products Research Laboratory, publication date unkown.
The Fundamental Properties of Paper Related to its Uses, vol. 1, B. Norman and D. Wahren, Swedish Forest Products Research Laboratory, Stockholm, Transactions of the Symposium held at Cambridge: Sep., 1973.
M/K Systems, Inc. advertisement, "Portable On-Line Formation Tester", undated.
Lippke Formation Sensor, Pulp & Paper Monthly, Sep. 19, 1986.

Primary Examiner—Richard A. Rosenberger
Attorney, Agent, or Firm—Spensley Horn Jubas & Lubitz

[57] ABSTRACT

A device for characterizing the formation of a sheet material is described. The device comprises a basis weight sensor for measuring the basis weight of the sheet material as the material passes through the sensor and signal processing circuitry which receives a signal from the basis weight sensor indicative of the measured basis weight and which produces three types of outputs, which outputs characterize: (1) the magnitude of variation in the sheet basis weight; (2) the strength of the weakest portion or portions of the sheet; and (3) the size of the flocs comprising the sheet. The basis weight sensor includes a light pipe which is held against the sheet, as the sheet moves through the sensor, and which directs a small spot of light transmitted through the sheet to a light detecting device. The magnitude of variation in the sheet basis weight is computed to be proportional to the true root-mean-square variation in the basis weight of the sheet.

26 Claims, 2 Drawing Sheets

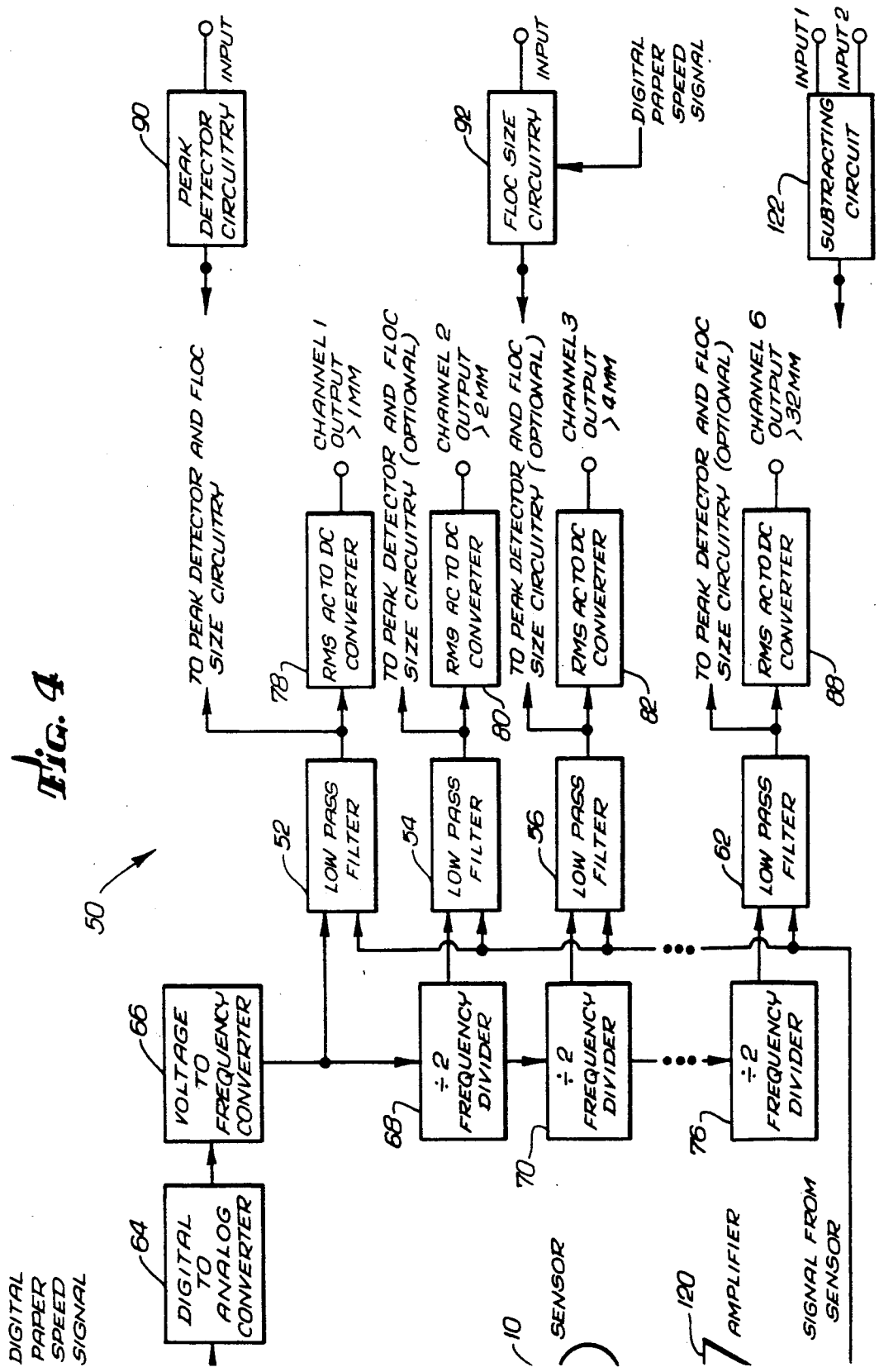

ON-LINE SHEET FORMATION CHARACTERIZING METHOD AND DEVICE

BACKGROUND OF THE INVENTION

This invention relates to a device and method for characterizing the quality of a sheet of paper, and more specifically, to a device and method which measure the distribution of cellulose fibers in a sheet of paper by monitoring the variations in the intensity of a narrow beam of light transmitted through the sheet as the sheet moves perpendicularly through the beam.

Paper is produced from a suspension of fibers. These fibers are usually made of cellulose, derived mainly from wood and rags. The evenness of the distribution of these fibers in a sheet of paper is of paramount importance to the optical, mechanical and printing properties of the sheet. Therefore, one of the chief goals for a paper maker is to develop a paper making process and adjust the parameters of the process to achieve as even a "basis weight" or distribution of these fibers in the finished sheet material as possible. In the paper making art, the term "basis weight" refers to the weight of the paper-forming fibers per unit area of the sheet surface. When the fibers are distributed evenly and the paper has a uniform basis weight, the sheet of paper will have its greatest strength, will look and feel smooth, and will be receptive to sharply defined lines of print. Conversely, local variations in the basis weight will yield a sheet having poor strength. This is because stress is concentrated in the areas of the sheet having fewer fibers, so that these areas of the sheet tear first. Furthermore, sheets having uneven basis weight may look and feel rough and will blur printed lines.

To charcterize the quality of a sheet of paper, paper makers refer to the "formation" of the sheet. There is, apparently, no standard definition of "formation." However, for the present purpose "formation" will be defined as the manner in which fibers forming a paper sheet are distributed, disposed and intermixed within the sheet. In all paper sheets, the sheet-forming fibers are, at least to a certain extent, unevenly distributed in bunches called "flocs." However, sheets of paper having generally evenly distributed, intertwined fibers are said to have good formation. Conversely, when the fibers forming the sheet are unacceptably unevenly distributed in flocs, the paper sheet is grainy rather than uniform and is said to have poor formation.

A variety of devices exist for measuring various characteristics of the formation of paper sheets. In one such device, called a basis weight sensor (or microdensitometer, a beam of light is transmitted through the sheet as the sheet passes perpendicularly through the beam. The intensity of the beam is measured by a light detector after the beam is transmitted through the paper sheet. This light detector is positioned on the opposite side of the sheet from the light source. The light detector produces an electrical signal indicative of the intensity of the transmitted beam. As the basis weight of the portion of sheet through which the light beam is passing increases, the intensity of the beam transmitted through the sheet decreases. Thus, the electrical signal from the light detector is indicative of the basis weight of the sheet.

As previously mentioned, the fibers forming every sheet of paper tend to congregate in flocs. In any one sheet, these flocs will have a variety of sizes. Thus, as the paper moves perpendicularly through the light beam, the electrical signal produced by the light detector will be modulated at a plurality of frequencies corresponding to the distribution of floc sizes and also to the speed with which the paper sheet moves through the light beam. As the sheet speed increases, the frequency with which the flocs modulate the electrical basis weight signal increases. Similarly, smaller flocs modulate the signal at higher frequencies than larger flocs. The amplitude of these modulations corresponds to the local variations in basis weight or, what amounts to the same thing, the local variations in the distribution of the fibers forming the flocs.

In one technique, the formation characterizing device displays the average peak-to-peak variation in the electrical signal produced by a basis weight sensor. The average peak-to-peak value of the electrical signal is said to indicate the magnitude of variations in the the basis weight of the sheet. However, for the reasons discussed below, this technique may give a false indication of the sheet formation.

In many instances, the paper maker will want to make a sheet having as even a fiber distribution as possible, i.e. one having good formation. To accomplish this, the paper maker will want to know, not only the magnitude of the variations in basis weight, but also the size distribution of the flocs. The paper maker will also want to know the strength of the lowest basis weight portions of the sheet. However, the previously described technique, which yields only the average peak-to-peak value of the basis weight signal, gives no indication of the size of the flocs creating these variations in the basis weight signal or the strength of the weakest areas of the sheet. Thus, this technique fails to completely characterize sheet formation.

In another technique for characterizing sheet formation, a beta radiograph is made of a sample sheet of paper. Light is then passed through or reflected off of the radiograph. Variations in the intensity of a narrow beam of this light are converted into an electrical signal as the radiograph moves, at a uniform speed, perpendicularly with respect to the beam. A graphical display is produced of the amplitude of the modulations of this electrical signal as a function of the wavelengths comprising the signal. This display is called a wavelength power spectrum. FIG. 1 illustrates one such display for several grades of paper having good, intermediate and poor formation. This technique has been discussed in great detail by Norman and Wahren in a number of papers, including their symposium paper "Mass Distribution and Sheet Properties of Paper".

For some commercial paper manufacturing situations, the Norman and Wahren technique may be inappropriate. As illustrated in FIG. 1, at wavelengths below about one millimeter, there is little difference between the wavelength power spectra of a well-formed sheet and a poorly-formed sheet. However, from wavelengths of about one millimeter to thirty-two millimeters, significant differences exist. Thus, the Norman and Wahren technique produces more information than may be necessary for the paper maker to determine formation of a sheet. Another possible disadvantage of this technique is that it provides so much information that its interpretation may be difficult for the non-expert. In many commercial manufacturing situations, the paper maker may prefer a device and technique which provides him or her with only a few numbers, which together completely characterize the formation of the sheet, rather than an entire spectral display. Moreover, this technique, like the previously described technique for measuring the average peak-to-peak value of a basis weight signal, fails to provide the paper maker with an indication of the strength of the weakest portions of the sheet. Thus, even if both techniques are used simultaneously, the paper maker is still not provided with all the information necessary to completely characterize sheet formation.

SUMMARY OF THE INVENTION

The present invention is directed to a method and device which provide a set of electrical output signals indicative of the following sheet formation parameters: (1) the magnitude of the variations in the basis weight of the sheet caused by flocs of predetermined minimum sizes or range of sizes; (2) the strength of the weakest portion or portions of the sheet; and (3) the size of the flocs forming the sheet. These output signals may be converted into numerical values and displayed to the paper mill operator. The operator can then use these numerical values to monitor the formation of the manufactured sheet and adjust the parameters of the paper making process to achieve a paper sheet having the desired characteristics. Alternatively, these electrical output signals can be fed into a computer or other device which would then use these output signals to automatically adjust the paper making process to achieve paper having the desired characteristics.

The device of the present invention includes a basis weight sensor for accurately measuring local variations in the basis weight of a sheet of paper. The sensor includes a light beam source, which is disposed on one side of the sheet, and a "receiver", disposed on the other side of the sheet opposing the light beam source. The receiver includes a light pipe, such as a narrow sapphire rod. One end of the rod abuts against the sheet on the opposite side of the sheet from the light source. As the sheet passes through the sensor perpendicular to the light beam, the sheet is held against the end of the rod so that only light which passes through the sheet can enter the rod. This rod directs at least a portion of the light beam to a light detecting device such as a photodiode. The photodiode then produces an electrical output porportional to the intensity of the light beam after the beam is transmitted through the sheet.

As the sheet of paper passes through the basis weight sensor local variations in the basis weight of the sheet create variations in the intensity of the light beam transmitted through the sheet. The light detecting device in the receiver portion of the sensor produces an electrical signal proportional to the intensity of the transmitted beam and hence inversely proportional to the basis weight of the portion of the sheet through which the detected portion of the beam is passing. Because paper consists of flocs of a variety of sizes, the electrical signal from the sensor is modulated at number of frequencies as the paper sheet passes between the light source and receiver halves of the sensor. These frequencies are dependent upon both the speed with which the paper passes through the sensor and the size of the various flocs forming the sheet. However, the signal processing circuits of the present invention account for changes in the speed with which the paper passes through the sensor. Thus, the output signals characterizing formation are independent of the paper speed.

The signal processing circuitry of the present invention has a plurality of electrical channels. Each channel processes basis weight signals from the basis weight sensor corresponding to a different predetermined minumum floc size, and floc sizes larger than that minimum. This is accomplished by placing a low pass filter at the input end of each channel. The signal from the basis weight sensor is fed into each of these low pass filters. However, the low pass filter of each succeeding channel has a cutoff frequency lower than that of the low pass filter in the preceding channel. In addition, the cutoff frequency for each of these low pass filters is variable and is controlled to be proportional to the speed with which the paper passes through the sensor. Thus, the cutoff frequency for the low pass filter of each channel corresponds to flocs of a particular predetermined minimum size and continues to correspond to flocs of this predetermined minimum size even when the speed with which the paper moves through the sensor is changed.

The output of each low pass filter is directed to a separate AC to DC converting circuit which converts the filtered signal from the associated low pass filter to a DC output proportional to the root-mean-square (hereinafter "RMS") value of the signal from the low pass filter. The output of each AC to DC converter therefore indicates the magnitude of the variations in the basis weight of the sheet created by flocs of a certain minimum size (i.e. the flocs modulating the basis weight signal at a frequency just below the cutoff frequency) and all flocs larger than that minimum size.

Additionally, the signal from the low pass filter of the first channel (the first channel low pass filter has the highest cutoff frequency) can be directed to a peak detector circuit. This circuit can be made to indicate the maximum intensity of the basis weight signal over a predetermined length of paper which passes through the basis weight sensor or the average of several signal peaks. A more intense transmitted light beam corresponds to a lower basis weight. Therefore, when the peak detector is made to indicate the maximum intensity of the basis weight signal, the magnitude of the output of the peak detector circuit characterizes the strength of weakest point of the sheet. Alternatively, when the peak detector circuit is made to indicate the average of several signal peaks, then the output of this circuit characterizes an average of the strengths of several of the weakest points in the sheet.

Moreover, the signal from the low pass filter of the first channel can also be directed to a floc size measuring circuit. The floc size measuring circuit includes a comparitor circuit which compares the value of the signal from the output of this low pass filter to a value indicative of the average basis weight of the sheet. The output from the comparitor circuit indicates the rate at which the signal from the first channel low pass filter achieves a value corresponding to the average basis weight of the sheet. If the signal from the first channel low pass filter only relatively rarely crosses the line corresponding to the average basis weight, then the sheet is composed of flocs of relatively large size. Alternatively, if the basis weight signal frequently crosses the average basis weight line, then the sheet is made of relatively small flocs. Thus, since the speed with which the paper sheet passes through the basis weight sensor is known, the floc size measuring circuit can compute, from the sheet speed and the output from the comparitor circuit, the size of the flocs forming the sheet.

Each of the three parameters discussed above—the magnitude of variation in the basis weight, the strength of the weakest portion or portions of the sheet and the floc size—relate to the formation or evenness of distribution of the fibers comprising the paper sheet. Since, as previously mentioned, the formation of a sheet of paper is of paramount importance to its optical, mechanical and printing properties, a paper maker can use the three types of electrical output signals of the present inventive device to help achieve an even distribution of fibers, and hence a well-formed paper sheet.

BRIEF DESCRIPTION OF THE DRAWINGS

FIG. 4 illustrates a block diagram of one embodiment of the circuitry of the present invention used to process signals from the basis weight sensor of FIG. 2.

DETAILED DESCRIPTION OF THE PREFERRED EMBODIMENT

A. The Basis Weight Sensor

Figure 2:
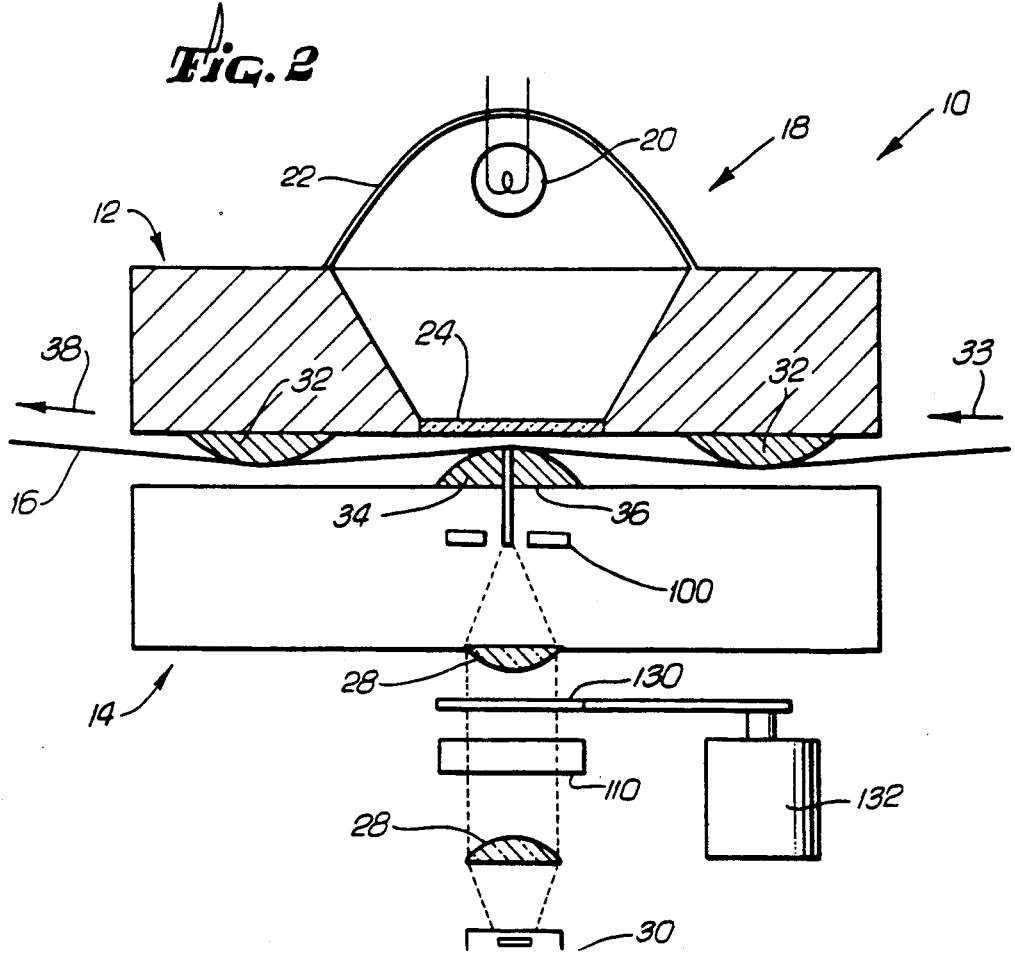
FIG. 2 illustrates one embodiment of the basis weight sensor of the present invention.

FIG. 2 illustrates a presently preferred embodiment of the basis weight sensor 10 of the present invention. This sensor 10 can be considered as consisting of two halves, a "source" half 12 and a "receiver" half 14. The source half 12, disposed on one side of the sheet of paper 16, directs a beam of light through the sheet 16 whose formation is to be determined. The receiver half 14 is disposed on the opposite side of the sheet 16 and produces an electrical signal porportioned to the intensity of the light which is transmitted through the sheet 16. The source half 12 includes a light source 18, such as a high intensity incandescent lamp 20, and a reflector 22 for directing the beam of light from the lamp 20 toward the sheet 16. As the light travels toward the sheet 16, it passes through a diffuser 24 which randomizes the direction of the photons as the beam passes through it. It is important to use a diffuse source of light. If a non-diffuse source of light is used, the receiver half 14 of the sensor 10 may measure variations in the intensity of the transmitted beam caused by variations in the reflectance of the sheet surface to light coming from one particular direction, rather than variations in transmitted light intensity caused by local variations in basis weight of the sheet 16.

The receiver half 14 of the sensor 10 includes a 1 mm. diameter sapphire light pipe 26 for directing a small spot of the diffuse light beam which is transmitted through the sheet 16 toward a lens system 28. This lens system 28 focuses the light from the light pipe 26 onto a light sensitive silicon photodiode 30. The photodiode 30 produces an electrical output signal proportional to the intensity of the spot of transmitted light.

It is important that the sheet 16 be held firmly against the end of the light pipe 36 as the sheet passes through the sensor 10 so that any light impinging upon the end of the light pipe 36 must have traveled through the sheet 16. To accomplish this goal, the source half 12 of the formation sensor 10 is formed with protrusions 32, called "skid plates", on opposite sides of the light pipe 26. In addition, the end of the light pipe 36 extends toward the sheet 16 and is protected by another skid plate 34 surrounding the light pipe 26 such that the paper sheet 16, travelling in the direction of the arrows 38 between the source and receiver halves of the sensor 10, is held by the skid plates 32, 34 against the end of the light pipe 36.

As the paper sheet 16 passes between and rubs against the skid plates 32, 34 and the end of the light pipe 36, the paper will tend to wear away the skid plates and the end of the light pipe 36. The skid plates 32, 34 are therefore constructed of an abrasion resistant material such as steel alloys and the light pipe 26 is made of sapphire or some other similarly transparent but abrasion resistant material.

B. The Signal Processing Circuitry

As previously mentioned, the basis weight sensor 10 produces an electrical signal the magnitude of which is inversely proportional to the basis weight of the portion of the sheet 16 through which the detected spot of the light beam transmitted. The sheet 16 is formed from flocs so that the transmitted beam intensity, and hence the sensor signal, varies as the paper sheet 16 passes through the sensor 10. The sensor signal is then amplified and the amplified sensor signal is fed to the signal processing circuitry. This circuitry is designed to process the sensor signal to yield electrical output signals indicative of: (1) the magnitude of the variations in basis weight of the sheet caused by flocs of predetermined minimum sizes or range of sizes; (2) the strength of the weakest portion or portions of the sheet; and (3) the size of the flocs forming the sheet.

A presently preferred embodiment of the signal processing circuitry 50 is shown in block diagram form in FIG. 4. This signal processing circuitry 50 comprises a plurality of low pass filters 52-62. Each filter 52-62 is associated with a particular electrical "channel". Each channel includes one of these low pass filters 52-62 and an RMS-AC to DC converter 78-88. The device of the present invention may have any number of channels (channels 4-5 are omitted to simplify the figure). In the embodiment of FIG. 4, the device has six channels. Each of the six low pass filters 52-62 receives two input signals. The first input signal to each of the six low pass filters 52-62 comes from the previously described basis weight sensor 10. This signal is directed to the first input of each low pass filter 52-62.

The cutoff frequency for each low pass filter 52-62 is proportional to the frequency of a second input signal. The frequency of the second input signal is not the same for each low pass filter 52-62. Instead, the frequency of the second input to each low pass filter 52-62 is one-half of the frequency of the signal fed to the second input of the low pass filter of the preceding channel. Thus, the cutoff frequency of the first channel low pass filter is highest and the cutoff frequency of the sixth channel low pass filter 62 is lower than the cutoff frequency of any of the other low pass filters 52-62. In other words, the first channel low pass filter 52 passes a signal from the basis weight sensor 10 the highest frequency component of which corresponds to a certain minimum floc size. The sensor 10 cannot sense changes in basis weight that occur in less than 1 mm since the light pipe 26 (FIG. 2) of the basis weight sensor 10 has a 1 mm. diameter. Thus, the highest frequency basis weight signal sent to the low pass filters corresponds to 1 mm. flocs. Therefore, in the present embodiment, the frequency of the signal sent to the second input of the low pass filter 52 of channel 1 is adjusted so that that this low pass filter 52 has a cutoff frequency corresponding to variations in the basis weight caused by 1 mm. flocs. The frequency of the signal sent to the second inputs of the low pass filters 54–62 of channels 2–6 is adjusted so that the cutoff frequencies of these low pass filters 54–62 correspond to floc sizes of 2 mm, 4 mm, 8 mm, 16 mm, and 32 mm, respectively. The frequency of the second input to each low pass filter 52–62 is also proportional to the speed with which the paper passes through the sensor 10. Thus, the cutoff frequency of each low pass filter 52–62 continues to correspond to a basis weight signal frequency characteristic of flocs of the above-mentioned sizes, even when of the speed with which the paper sheet passes through the sensor 10 changes.

In the present preferred embodiment, the second input signal to each low pass filter 52–62 is derived by first measuring the speed with which the paper sheet passes through the sensor 10. Devices which measure the speed of a paper sheet are well known in the art. Many modern paper mills are highly automated and include a computer which monitors and controls various parameters of the paper making process. Thus, in the present preferred embodiment, a digital signal from the mill's computer indicative of the paper speed is conveniently used to control the cutoff frequency of the low pass filter 52–62 of each channel. This digital speed signal is directed to a digital to analog converter 64 which receives the digital speed signal and outputs a voltage proportional to the paper speed. This voltage is then input to a voltage to frequency converter 66 (hereinafter "VFC"). The VFC 66 then outputs a signal having a frequency which is porportional to the output voltage of the digital to analog converter 64 and hence to speed of the paper passing through the sensor 10. Each channel, except the first channel, includes a frequency divider 68–76. The signal from the VFC 66 is fed directly into the second input of the first channel low pass filter 52, and also into the frequency divider 68 of the second channel. The frequency divider 68 of the second channel divides the frequency of the signal received from the VFC 66 and the resulting lower frequency signal is fed to the second input of the low pass filter 54 of the second channel and also to the frequency divider 70 of the third channel. Thus, the second input to the low pass filter 52 of the first channel is at frequency X. Frequency X corresponds to the speed with which the paper passes through the sensor 10. Since divide-by-two frequency dividers are used in the present preferred embodiment, the frequency input to the low pass filter 54 of the second channel is at frequency X/2. The signal output by frequency divider 68 of the second channel is also fed the input of the frequency divider 70 of the third channel. Each succeeding channel 4, 5, and 6 also have frequency dividers, for example frequency divider 76, which receive the signal from the frequency divider of the preceding channel and output a signal at one-half the frequency of the received signal. Thus, the frequency of the signal fed to the second input of the low pass filter 56 of the third channel is at frequency X/4, the frequency of the signal fed to the second input of the fourth channel low pass filter (not shown) is X/8, etc. In this way, the output of the low pass filter 52 of the first channel comprises frequencies corresponding to floc sizes greater than or equal to a minimum size, i.e. 1 mm. The highest frequency passed through to the output of the low pass filter in each succeeding channel corresponds to floc sizes of increasingly larger minimum size, i.e. 2 mm, 4 mm, 8 mm, 16 mm and 32 mm. The output of each channel's low pass filter 52–62 is then processed to indicate various formation parameters of the sheet being sensed for floc sizes at and above the minumum floc size for the particular channel.

To derive an output signal indicative of the magnitude of the variations in the basis weight of the sheet, the output of each low pass filter 52–62 is directed to an associated AC to DC converter 78–88. Each AC to DC converter 78–88 produces a DC voltage equivalent to the RMS value of the AC signal output from the associated low pass filter 52–62. The RMS value of the DC voltage produced by each AC to DC converter 78–88 is proportional to the magnitude of variation in the basis weight of the sheet caused by flocs of a particular minimum size. Since the cutoff frequency of the low pass filters 52–62 in each succeeding channel is set to succeedingly lower frequencies, the magnitude of the RMS DC output voltage of each succeeding channel corresponds to the magnitude of variation in the basis weight of the sheet caused by succeedingly larger minimum floc sizes.

In certain situations, the mill operator will want to know the magnitude of the basis weight variations in the sheet caused by flocs in a particular size range. The device of the present invention can provide this information by simply subtracting the RMS DC output of the AC to DC converter of one channel from the RMS DC output of the AC to DC converter of another channel. The difference between the value of these outputs corresponds to the magnitude of the basis weight variations caused by flocs in the size range between the cutoff frequencies of the low pass filters of the two channels.

A subtracting circuit 122 may be provided to receive, at inputs 1 and 2, the output of any two selected AC to DC converters. This subtracting circuit produces an output voltage corresponding to the difference between the outputs of the two selected AC to DC converters. Alternatively, if the output of the various AC to DC converters are numerically displayed, then the paper mill operator can obtain the difference between any two such outputs by subtraction. For example, to determine the magnitude of the basis weight variations caused by flocs between 4 mm and 8 mm, the paper mill operator simply subtracts the value of the output of the fourth channel AC to DC converter from the value of the output of the third channel AC to DC converter.

Many standard "RMS" AC to DC converters actually measure the peak-to-peak voltage of the incoming signal and then provide an output DC signal which corresponds to the true RMS value of the input signal only if the input signal is sinusoidal. However, the basis weight signal waveshape is generally not sinusoidal. It is, therefore, usually important that the AC to DC converters 78–88 of the present invention output a DC voltage corresponding to the true RMS value of the basis weight signal, otherwise the output signal of these AC to DC converters 78–88 may provide an inaccurate measure of the basis weight variations.

The use of true RMS-AC to DC converters is particularly important when the output of the converter of one channel is subtracted from the output of a converter of another channel to thereby determine the contribution to the basis weight variations caused by flocs in a particular size range. Flocs of different sizes may cause the same peak-to-peak changes in the basis weight signal, even though their contribution to the RMS value of the basis weight signal is different. Thus, subtracting an AC to DC converter output derived from a basis weight signal containing frequencies corresponding to, for example, 8 mm. minimum floc sizes, from one corresponding to 4 mm. minimum floc sizes, should and would yield a signal indicative of the contribution to basis weight variation caused by flocs in the 4-8 mm size range, if true RMS AC to DC converters are used. However, if the "RMS" signal is actually derived from a measurement of the peak-to-peak signal value, and flocs of different sizes are causing the same peak-to-peak change in basis weight signal, then the difference between the outputs of the two AC to DC converters would be zero. However, this would not be a correct indication of the contribution to basis weight variation caused by the flocs in the 4-8 mm range. Thus, the use of standard peak-to-peak AC to DC converters may give false readings when used in the device of the present invention.

The second parameter, indicative of the strength of the weakest portion of the sheet, is obtained by feeding the output of the low pass filter 52 of the first channel to the input of a peak detecting circuit 90. Since, as previously mentioned, the magnitude of the intensity of the transmitted beam is inversely proportional to the basis weight of the sheet, the magnitude of the AC signal at the output of this low pass filter 52 will also be inversely proportional to the local basis weight of the portion of the sheet then being sensed by the sensor 10. The peak detecting circuit 90 may be designed to provide a DC output proportional to the largest voltage peak which passes through the first channel low pass filter 52 in a predetermined time period or for a predetermined length of sheet passing through the sensor 10. The magnitude of this signal indicates the weakest point in the sheet. Alternatively, the peak detector circuit 10 may also be designed to produce an output proportional to the average of several signal peaks over a set period of time or length of sheet passing through the sensor 10. In this latter case, the output of the peak detector circuit 90 would characterize an average weak spot in the sheet.

The signal processing circuits 50 of the present invention may provide the paper manufacturer with yet a third output signal indicative of another characteristic of the paper sheet—the average floc size. To obtain this parameter, the output of the low pass filter 52 of the first channel is fed to a floc size measuring circuit 92. This circuit 92 counts the number of times, during a predetermined time interval, that the output signal from the low pass filter 52 of the first channel achieves a value corresponding to the average basis weight of the sheet. The frequency with which this signal crosses this average basis weight value divided by the speed of the paper through the sensor indicates the average size of the flocs forming the sheet. The floc size measuring circuit 92 electronically performs this division and outputs a signal corresponding to the average floc size. For example, if the paper sheet is moving at 1000 m/min and the output from the low pass filter of the first channel achieved a value corresponding to the average basis weight 3333 times in a one second time interval, then the average floc size of the sheet is 10 mm (1000 m/min.1 min/60 sec.1 sec/3333 crossings. 2 crossings/floc). Thus, by sensing the basis weight of the paper sheet along a line or curve (hereinafter collectively "line") along the sheet surface, the device and method of the present invention can provide the paper manufacturer with an output signal indicative of the size of the flocs forming the sheet.

C. Use and Calibration of the Device

In a paper mill, paper is typically produced in sheets about 25 feet wide. To characterize the entire sheet, one basis weight formation sensor can be moved or "scanned" back and forth in the "cross direction" of the sheet (i.e. across the width of the sheet) as the sheet moves along in the "machine direction" (i.e. the lengthwise direction). Alternatively, a plurality of sensors can be scanned back and forth in the cross direction across only a part of the width of the sheet. If, for example, 50 basis weight sensors are used on a 25 foot wide sheet, then each sensor would be made to scan back and forth across a 6 inch wide strip of the sheet. Typically, paper mills produce such sheets at about more than 1000 feet per minute and the back and forth scanning speed of the sensor in the present embodiment may be set at 60 feet per minute. Thus, the cutoff frequency of the low pass filters may be made proportional only to the speed with which the sheet moves in the machine direction without introducing substantial error into the output readings. The additional contribution to the speed with which the paper moves through the sensor, caused by the cross directional movement of the sensor, is minimal, and can usually be ignored.

For the receiver part of the basis weight sensor 14 (FIG. 2) to operate properly, the light from the source side of the sensor 12 must be aligned directly opposite the sheet from the receiver 14. However, the two halves of the basis weight sensor 10 cannot be directly connected together since the paper sheet 16 passes between these two halves. A number of different mechanisms can be used to keep the two halves of the sensor 10 directly opposite to each other as they scan back and forth across the sheet 16. One such device, for example, consists of two tracks (not shown), one on each side of the sheet 16. The source side of the sensor 12 rides on one of the tracks and the receiver side of the sensor 14 rides on the other track. A gear or pulley system moves the two halves of the sensor in unison and opposite each other back and forth across the width of the sheet 16. In this way, the source 12 and receiver 14 halves remain directly opposite each other without the necessity of penetrating the sheet with a connecting member.

Figure 1:
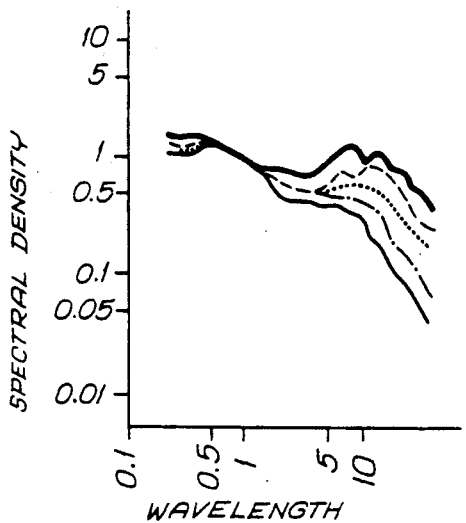
FIG. 1 illustrates wavelength power spectra for several different grades of paper.
Figure 3:
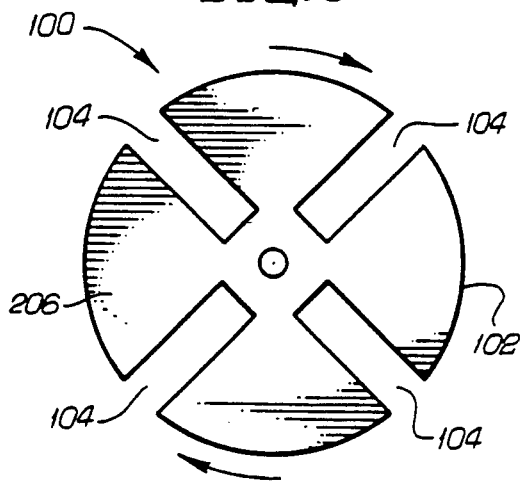
FIG. 3 illustrates a chopper wheel for calibrating the device of the present invention.

Calibration of the device of the present invention may be done "off sheet", i.e. without having a paper sheet between the two sensor halves. To calibrate the outputs of the low pass filters, a chopper wheel 100 (FIGS. 2-3) is positioned between the sensor's light source 18 and photodiode 30. In the present embodiment, the chopper wheel 100 is positioned at the base of the light pipe 26. The chopper wheel 100 is made from a circular disc 102 of opaque material having a plurality of radial slots 104 positioned around the wheel 100. The chopper wheel 100 is driven at a known rotational speed so that the photodiode 30 receives pulses of light. The pulsing rate is determined by the predetermined speed of rotation of the wheel 100. The paper speed signal can then be set so that the low pass filters of all channels 52-62 (FIG. 4) will transmit signals to the associated RMS-AC to DC converters 78-88. Then, by inputting successively lower paper speeds, the low pass filter cutoff frequencies can be calibrated. For example, if a chopper wheel 100 with four radial slots 104, like that of FIG. 3, is rotated at a speed of 142.5 rotations per second, the chopper wheel 100 will modulate the light impinging upon the light detector at 570 Hz. If the paper speed signal from the VFC 66 is faster than 1094 m/min., then all channels will see the signal. However, as the paper speed drops below 1094 m/min., only channels 1-5 will provide an output. Further decreases in the paper speed signal will cause additional low pass filters to cutoff the signal from the basis weight sensor 10.

Any device which modulates the intensity of the light reaching the light detector can be used other than a chopper wheel 100. For example, a tuning fork, the arms of which oscillate into and out of the light beam at a known frequency, could be used in place of a chopper wheel 100.

Different types of paper will preferentially absorb or reflect certain frequencies of light. Therefore, to optimize the sensitivity of the basis weight sensor to changes in basis weight, an optical band pass filter 110 (FIG. 2) may be placed in the path of the light beam. This band pass filter 110 will preferentially pass light of certain frequencies to the photodiode 30.

To properly measure variations in the basis weight of the sheet, it is important that the amplified basis weight signal from amplifier 120 (FIG. 4) be inversely proportional to the basis weight of the sheet. To ensure that the amplitude of the basis weight signal fed to the low pass filters 52-62 responds linearly to changes in basis weight, the amplified detector signal can be measured with and without a neutral density filter 130 (FIG. 2) placed in the path of the light beam. The neutral density filter 130 attenuates the beam intensity by a known percentage. The amplitude of the amplified basis weight signal should be measured first while the pivot 132 has pivoted the neutral density filter 130 out of the path of the beam. Then, the neutral density filter 130 is pivoted, by the pivot 132, into the path of the beam. While the neutral density filter 130 is in the beam path, the amplified basis weight signal should again be measured. Non-linearities in the output of the sensor can then be compensated for by adjusting the amplifier 120 (FIG. 4) so that the change in the amplitude of the amplified basis weight signal caused by placing the neutral density filter 130 in the beam path linearly corresponds to the known change in the light beam intensity caused by positioning the neutral density filter 130 in the beam path.

In a device constructed according to the present invention, for example as described in the presently preferred embodiment above, a paper manufacturer is provided with output signals which correspond to three important parameters in paper manufacturing: (1) the magnitude of the variations in the basis weight of the sheet caused by flocs of predetermined minimum sizes or range of sizes; (2) the strength of the weakest portion or portions of the sheet; and (3) the size of the flocs forming the sheet. By monitoring these parameters, the paper manufacturer can adjust his or her paper making processes to provide a sheet of paper having evenly distributed fibers. Such a well-formed sheet will have high strength, good optical and textural properties and good printing quality.

One preferred embodiment of the basis weight sensor and signal processing circuitry have been described. Nevertheless, it will be understood that various modifications may be made to the basis weight sensor or signal processing circuitry described herein without departing from the spirit and scope of the invention. For example, where the diameter of the light pipe of the basis weight sensor corresponds to the smallest floc size which the paper manufacturer desires to examine, then the highest frequency component of the signal from the basis weight sensor will correspond to flocs having a minimum size equal to the diameter of the light pipe. Thus, a low pass filter in the first channel is not necessary if one only wanted to examine signals from the first channel corresponding to flocs having a minimum size equal to the diameter of the light pipe. Instead, the amplified basis weight sensor signal can be fed directly to the RMS-AC to DC converter of the first channel. Furthermore, the signal processing circuitry may be modified, if desired, such that the output signal from the low pass filter of a channel other than the first channel low pass filter is sent to the peak detector circuitry or to the floc size measuring circuit. Alternatively, the signal processing circuitry may be so constructed that the input to the peak detector and floc size measuring circuits can be selected from the low pass filter of any desired channel. This is indicated in FIG. 4 as an optional design. Moreover, sheet materials other than paper may be passed through the sensor and characterized by the device of the present invention. Thus, the present invention is not limited to the preferred embodiments described herein, nor is it limited strictly to use with paper.

What is claimed is:

1. A basis weight sensor, comprising:
   a) a light source;
   b) light detector means for detecting light transmitted from the light source and producing a signal indicative of the intensity of the detected light;
   c) a light pipe, disposed between the light source and the light detector means, said light pipe having a first end directed toward said light source to receive light and a second end, opposite said first end, directed toward said light detector means, such that the light pipe guides light from the light source to the light detector means;
   d) holding means for holding a moving sheet of material against said first end of the light pipe; and
   e) modulating means for modulating, at a predetermined frequency, the intensity of the light detected by the light detector means.

2. The basis weight sensor of claim 1, wherein the modulating means includes a chopper wheel, disposed between the light source and the light detector, the chopper wheel being formed of a rotatable opaque disc having at least one opening therethrough, said opening being spaced from the center of the disc.

3. The basis weight sensor of claim 1, wherein said light pipe is made of sapphire.

4. A sheet formation characterizing device, comprising:
   a basis weight sensor means for sensing the basis weight of a portion of a sheet of material and producing a basis weight signal indicative of the basis weight of the portion of the sheet; and
   a first channel including a first AC to DC converter for receiving the basis weight signal, determining the true root-mean-square value of the basis weight signal, and generating an output signal indicative of the true root-mean-square value of the basis weight signal.

5. The device of claim 4, wherein the first AC to DC converter generates an output signal equal to the true root-mean-square value of the basis weight signal.

6. A sheet formation characterizing device, comprising:
   a basis weight sensor means for sensing the basis weight of a portion of a sheet of material and producing a basis weight signal indicative of the basis weight of the portion of the sheet;

a first channel including a first AC to DC converter for receiving the basis weight signal and generating an output signal indicative of the true root-mean-square value of the basis weight signal; and at least one additional channel including a low pass filter having an input for receiving the basis weight signal from the basis weight sensor and an output, wherein the low pass filter filters out the frequency components of the basis weight signal which are above a predetermined cutoff frequency and passes the filtered basis weight signal to the output, each additional channel further including a second AC to DC converter operatively coupled to the output of the low pass filter, the second AC to DC converter generating a DC output signal indicative of the root-mean-square value of the filtered basis weight signal.

7. The device of claim 6, further comprising means for varying the cutoff frequency of the low pass filter of each additional channel directly with respect to the speed at which the sheet moves through the basis weight sensor.

8. The device of claim 6 or claim 7, having a plurality of additional channels, and wherein the cutoff frequency of the low pass filter of each additional channel is different than the cutoff frequency of the low pass filters of each of the other additional channels.

9. The device of claim 8, further comprising means for selecting the output signal from two of the AC to DC converters and producing a signal indicative of the difference between the outputs of the selected AC to DC converters.

10. A sheet formation characterizing device, comprising:

basis weight sensor means for sensing the basis weight of a portion of a sheet material and producing a basis weight signal indicative of the basis weight of the portion of the sheet;

a plurality of channels, wherein a first channel includes a first low pass filter for filtering out frequency components of the basis weight signal which are above a first predetermined cutoff frequency and for passing a first peak of the basis weight signal, and wherein a second channel includes a second low pass filter for filtering out frequency components of the basis weight signal which are above a second predetermined cutoff frequency and for passing a second peak of the basis weight signal; and peak detector means, operatively coupled to the basis weight sensor through the plurality of channels, for detecting the first and second peak and generating an output signal indicative of the value of the first and second peak of the basis weight signal received by the peak detector means during a predetermined time interval.

11. The device of claim 10, further comprising means for varying the cutoff frequency of the low pass filter of each channel with respect to the speed at which the sheet moves through the basis weight sensor.

12. A sheet formation characterizing device, comprising:

basis weight sensor means for sensing the basis weight of a portion of a sheet material and producing a basis weight signal indicative of the basis weight of the portion of the sheet; and floc size measuring means, operatively coupled to the basis weight sensor, for generating an output signal indicative of the number of times the basis weight signal received by the floc size measuring means achieves a predetermined value during a predetermined time interval.

13. A method for characterizing the formation of a sheet material, comprising the steps of:

measuring the variations in the basis weight of the sheet material;

determining the true root-mean square of the measured variations in the basis weight; and producing an output signal indicative of the true root-mean-square value of the measured variations in the basis weight on the sheet.

14. The method of claim 13, wherein the output signal is equal to the true root-mean-square value of the measured variations in the basis weight of the sheet.

15. A method for characterizing the formation of a sheet material, comprising the steps of:

modulating a first signal according to variations in the basis weight of a sheet material;

filtering the first signal to produce a plurality of filtered outputs, wherein each filtered output is derived from said first signal by filtering out all frequency components of the first signal above a predetermined frequency, and wherein the predetermined frequency is different for each filtered output; and varying the value of the predetermined frequency for each filtered output according to changes in a second signal.

16. The method of claim 15, further comprising the step of producing a separate DC output from each filtered output, each DC output being indicative of the root-mean-square value of a filtered output.

17. The method of claim 16, further comprising the steps of:

selecting two of the DC outputs; and subtracting the value of one of the selected DC outputs from the value of the other of the selected DC outputs.

18. The method of claim 15, wherein the second signal is a signal indicative of the speed of the sheet material.

19. A method for characterizing the formation of a sheet material, comprising the steps of:

modulating a signal based on variations in the basis weight of a sheet material;

filtering out frequency components of the basis weight signal which are above a first predetermined cutoff frequency and passing a first peak of the basis weight signal, and filtering out frequency components of the basis weight signal which are above a second predetermined cutoff frequency and passing a second peak of the basis weight signal; and producing an output indicative of the first and second peak of the modulated signal achieved during a predetermined time interval.

20. A method for characterizing the formation of a sheet material, comprising the steps of:

producing a first signal indicative of the variation in the basis weight of a sheet material along a line through the sheet;

producing a second signal indicative of the frequency with which the first signal achieves a predetermined value.

21. The method of claim 20, wherein the predetermined value is indicative of the average basis weight of the sheet material.

22. A formation sensor, comprising:
a) a source of diffuse light;
b) a light detector for detecting light transmitted from the source of diffuse light and producing a signal indicative of the intensity of the detected light;
c) a light pipe, disposed between the light source and the light detector, said light pipe having a first end directed toward the light source to receive light and a second end, opposite the first end, directed toward the light detector, such that the light pipe guides light from the light source to the light detector; and
d) holding means for holding a moving sheet of material against said first end of the light pipe.

23. The formation sensor sensor of claim 22, wherein the source of diffuse light is substantially greater in lateral extent, measured approximately perpendicularly to the axis of the first end of the light pipe, than the first end of said light pipe.

24. A sheet formation characterizing device, comprising:
a basis weight sensor for sensing the localized variations in the basis weight of a moving sheet material caused by flocs and producing a fluctuating basis weight signal indicative of the variations of the basis weight of the sheet; and
a plurality of electronic channels, each channel including a low pass filter having an output and an input operatively coupled to the basis weight sensor for receiving the basis weight signal from the sensor, wherein each low pass filter filters out the frequency components of the basis weight signal above a cut-off frequency and wherein each low pass filter passes the filtered basis weight signals to the associated outputs, each channel further including an AC to DC converter operatively coupled to the output of one of the low pass filters, each of the AC to DC converters generating a DC output signal indicative of the root-mean-square value of the filtered basis weight signal.

25. The device of claim 24, further comprising means for varying the cut-off frequencies of the low pass filters in response to changes in the speed at which the sheet moves through the device.

26. The device of claim 25, further comprising means for selecting the output signals from two of the AC to DC converters and producing a signal indicative of the difference between the outputs of the selected AC to DC converters.

* * * * *